United States Patent [19]

Blohm et al.

[11] Patent Number: 5,075,464
[45] Date of Patent: Dec. 24, 1991

[54] 17β-(CYCLOPROPYLAMINO)ANDROSTENE DERIVATIVES

[75] Inventors: Thomas R. Blohm, Cincinnati; Michael R. Angelastro, Loveland, both of Ohio

[73] Assignee: Merrell Dow Pharmaceuticals Inc., Cincinnati, Ohio

[21] Appl. No.: 366,564

[22] Filed: Jun. 14, 1989

Related U.S. Application Data

[63] Continuation-in-part of Ser. No. 41,172, Apr. 22, 1987.

[51] Int. Cl.$^5$ ............................................. C07J 41/00
[52] U.S. Cl. ................................... 552/522; 514/177; 514/182
[58] Field of Search .................. 260/397.3, 397.5; 514/177, 182

[56]  References Cited

U.S. PATENT DOCUMENTS 3,097,200  7/1963  Kincl ................................. 260/239.5
3,107,254  10/1963  Lednicer ........................... 260/397.3
4,477,445  10/1984  Philibert et al. .................... 514/182

FOREIGN PATENT DOCUMENTS 3159M  1/1964  France .
63/5728  6/1964  South Africa .
1027746  4/1966  United Kingdom .

OTHER PUBLICATIONS

Davis et al., *Chem. Soc., C, Org.*, 19, 1688 (1966).
B. J. Taylor, M. S. Thesis, Massachusetts Institute of Technology, 1985, pp. 2, 24–26.

*Primary Examiner*—C. Warren Ivy
*Assistant Examiner*—Celia Chang
*Attorney, Agent, or Firm*—John J. Kolano

[57] ABSTRACT

This invention is directed to 17β-(cyclopropylamino)androstenes and also to a method for using such compounds in the treatment of androgen-dependent disorders. The compounds are prepared by the hydride reduction of an appropriate steroidal imine or enamine.

4 Claims, No Drawings

17β-(CYCLOPROPYLAMINO)ANDROSTENE DERIVATIVES

The present application is a continuation-in-part of application Ser. No. 41,172 filed Apr. 22, 1987.

The present invention is directed to 17β-(cyclopropylamino)androstene derivatives and also to a method for using such compounds in the treatment of androgen-dependent disorders. More particularly, the present invention is directed to a compound having a formula selected from the group consisting of:

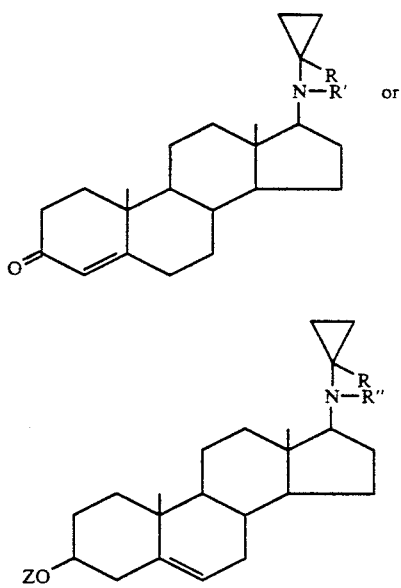

wherein R is hydrogen or methyl; R' is hydrogen, $C_1$-$C_4$ alkyl or cyclopropyl; R" is $C_1$-$C_4$ alkyl or cyclopropyl; Z is hydrogen, alkanoyl of 1–10 carbon atoms, cyclopentane-alkanoyl or benzene-alkanoyl wherein the alkanoxyl portion of the cyclopentane-alkanoyl or benzene-alkanoyl contains up to 4 carbon atoms. Examples of alkanoyl groups are acetyl, propionyl, butanoyl, and decanoyl; examples of the cyclopentane-alkanoyl and benzene-alkanoyl groups are cyclopentanepropionyl and benzenepropionyl. Preferred compounds are those which are 3-keto-steroids Acid addition salts of the aforesaid compounds with pharmaceutically acceptable acids are equivalent to the above amines for the purposes of this invention. Illustrative of such salts are the salts with inorganic acids such as, for example, hydrochloric, hydrobromic, sulfuric, phosphoric and like acids; with organic carboxylic acids such as, for examples, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acids.

The compounds of the present invention are conveniently prepared by the reduction of an appropriate steroidal imine or enamine, wherein the compound used is a 3-hydroxy or 3-alkanoyloxy-$\Delta^5$-steroid, with a hydride reducing agent. Where the starting material is an imine, the reaction can be illustrated as follows:

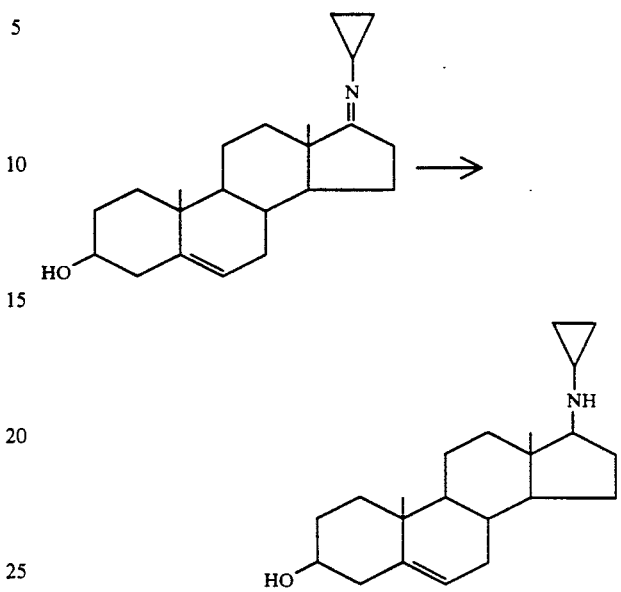

In this case, the reduction is carried out using a hydride reducing agent, preferably sodium borohydride, in an alkanol solvent. To obtain the compounds which contain an esterified 3-hydroxy group, the amine as shown above is reacted with carbobenzoxy chloride to give the corresponding N-carbobenzoxy compound This is then acylated using, for example, acetic anhydride to give the corresponding 3-acetoxy steroid. The N-carbobenzoxy protecting group is then removed by treatment with hydrogen bromide and acetic acid or by catalytic transfer hydrogenation. In either case, the product obtained is a secondary amine which can be converted to the corresponding N-methyl compound by treatment with formaldehyde and formic acid in an Eschweiler-Clarke reaction or by reaction with aqueous formaldehyde and sodium borohydride.

Those compounds wherein R' or R" is $C_{2-4}$ alkyl can be obtained from a 17-cyclopropylamino steroid. This is reacted, for example, with acetyl chloride to give the corresponding acetamide which is then reduced with sodium cyanoborohydride to give the N-ethyl compound. In those cases where the above reaction with acetyl chloride also gives the 3-ester, the ester group can be removed, after the reduction, by base hydrolysis such as a combination of potassium carbonate, methanol and tetrahydrofuran or by acid hydrolysis such as with hydrochloric acid. In the latter case, the hydrochloride salt is obtained.

The 3-hydroxy-$\Delta^5$-compound obtained above can be converted to the corresponding 3-keto-$\Delta^4$-compound by an Oppenauer oxidation using aluminum isopropoxide.

The imine starting material used in this process can be obtained by the reaction of dehydroepiandrosterone with the appropriate cyclopropylamine in refluxing methanol. The reaction is carried out in the presence of a dehydrating agent to remove water from the reaction mixture as it is formed.

When the reduction referred to initially is carried out on an enamine, borane is used as the reducing agent. The necessary enamine starting material is obtained by the condensation of dehydroepiandrosterone with an appropriate secondary amine such as dicyclopropylamine. The alcohol final product obtained in this process can be acylated with an appropriate anhydride, such as acetic anhydride, to give the corresponding 3-acetoxy compound or it can be oxidized in an Oppenauer oxidation to give the corresponding 3-keto$\Delta^4$-compound.

The present compounds are useful as inhibitors of steroid $C_{17-20}$ lyase and thus inhibit testosterone formation. Consequently, they are useful for treating various androgen-dependent disorders. The present invention thus also encompasses a method for treating androgen-dependent disorders which comprises administering to an individual suffering from such a disorder an effective amount of a compound of the present invention. More particularly, the present compounds are useful in the treatment of prostatic carcinoma, benign prostatic hyperplasia and virilism and hirsutism (in women).

It is well established that reduction of serum testosterone levels is useful in the treatment of many cases of prostatic carcinoma. In clinical practice, this has been accomplished by orchiectomy or by diethylstilbestrol treatment but the first approach is often psychologically unacceptable while a number of side effects are associated with the second approach. Thus, an alternative approach to testosterone reduction is desirable and this can be accomplished by the administration of the present compounds. To the extent that prostatic carcinoma is androgen-dependent, the present compounds would block the source of androgens and thus serve as an appropriate treatment for this condition.

The activity of the present compounds as inhibitors of steroid $C_{17-20}$ lyase was established using microsomal preparations of the steroid $C_{17-20}$ lyase enzyme from human or laboratory animal testis; human testes used for this purpose were obtained from therapeutic orchiectomies. The enzyme was incubated with NADPH and the test compound in the concentration range $5 \times 10^{-8}$M to $3 \times 10^{-6}$M and the extent of inhibition of the enzyme was determined with time-dependency of inhibition being established by a decline in enzyme activity with the time of exposure to the test compound. Time-dependency of inhibition often implies irreversible inactivation of the enzyme and irreversibility was specifically established by inability to restore enzyme activity by dialysis under conditions which maintained activity of native enzyme. When tested according to the above procedure using human enzyme, the compounds of the present invention were found to inhibit the enzyme in a time-dependent manner and irreversibly.

In the treatment of the various androgen-dependent disorders described earlier, the compounds of the present invention may be administered orally to the patient being treated to achieve the particular effect desired. The amount of compound to be administered will vary over a wide range and can be any effective amount. Depending on the patient to be treated, and the severity of the condition being treated, the effective amount of compound administered will vary from about 0.625 to 62.5 mg/kg of body weight per day and preferably from 5 to 30 mg/kg of body weight per day. Unit dosages for oral administration may contain, for example, from 25 to 500 mg of a compound of the invention. Alternatively, the present compounds can be administered by parenteral routes or by implants.

The compounds of the present invention also inhibit the synthesis of aldosterone and thus are useful for the treatment of conditions in which such inhibition would be desired. Thus, the indicated compounds are useful in the treatment of hyperaldosteronism and various conditions wherein a reduction of the excessive amount of aldosterone responsible for the condition would be beneficial. That is, they are useful in the general treatment of hyperaldosteronism and any associated hypertension, edema and/or sodium retention whether this is the result of some bodily disorder or whether it results from the administration of some agent. As a result of their effect on the factors responsible for edema and/or sodium retention, the indicated compounds would be useful as diuretic agents.

The activity of the indicated compounds as aldosterone inhibitors and, thus, their utility in treating hyperaldosteronism can be demonstrated by the following procedure which measures the inhibition of enzymes in the synthesis of aldosterone.

Young male Sprague-Dawley rats were maintained on a sodium-deficient diet for about two weeks prior to use. From these animals, adrenal capsule/glomerulosa homogenates were prepared (6 mg/ml) in pH 7.4 assay buffer [$MgCl_2$ 8.5 mM, $CaCl_2$ 2.7 mM, KCl 3.13 mM, NaCl 7.591 mM, TRIS 50 mM and 0.1% triethylamine] and centrifuged 500xg for 10 minutes.

Assays were conducted in 35 ml glass tubes maintained at 25° C. in a Dubnoff shaker with 95% $O_2$/5% $CO_2$. The tubes contained the following material: 100 μl of an NADPH+ generating system, 300 μl of adrenal capsular/glomerulosa cytosol, and 50 μl of test compound or buffer (control). After initial preincubation intervals of 20 minutes, the 10-minute assay was started by the addition of 50 μl of tritium-labelled substrate, i.e., 1 μM [$^3$H]-DOC. Reactions were quenched by the addition of 5 ml of ethyl acetate and non-radiolabelled steroids were also added. The samples were extracted twice with 5 ml of ethyl acetate and the solvent evaporated under nitrogen at 30°–40° C.

Residues were redissolved in methanol water (40:60) with 0.1% triethylamine and high performance liquid chromatography was used to separate products on a C18 reverse phase (5 μODS-Hypersil) column (4.6×250 mm, Shannon) with a 1 ml/min flow rate using an MeOH:$H_2O$ gradient (solvent A 10/90:solvent B 90/10).

Substrate remaining and products formed were monitored by UV absorbance at 246 nM and the amount of steroid compound present was quantified by [$^3$H] radioactivity. The concentration of compound to produce half-maximal inhibition ($IC_{50}$) of aldosterone formation from the 40 minute preincubation data was graphically estimated from a linear-log plot of percent inhibition vs. log of the compound concentration. The $K_i$ time-dependent inhibition and the $t_{1/2}$ for enzyme inactivation at infinite inhibitor concentration ($t_{50}$) was determined by the linear regression analyses of $t_{1/2}$ vs. $1/[I]$ data of Kitz-Wilson plots Using this procedure, the following results were observed:

| Test Compound | $IC_{50}$ (μM) | $K_i$ (μM) | $t_{50}$ (min) |
| --- | --- | --- | --- |
| 17β-(Cyclopropyl-amino)androst-4-en-3-one | 0.18 | — | — |
| 17β-[N-Methyl(cyclopropylamino)]androst-4-en-3-one | 0.13 | 0.14 | 15.4 |
| 17β-[N-Methyl(cyclopropyl-amino)]- | 0.35 | 0.35 | 9.0 |

| Test Compound | IC$_{50}$ ($\mu$M) | K$_i$ ($\mu$M) | t$_{50}$ (min) |
|---|---|---|---|
| androst-5-en-3$\beta$-ol | | | |

The above results demonstrate the effectiveness of the present 17-cyclopropylaminoandrostenes as inhibitors of aldosterone biosynthesis.

To achieve a particular aldosterone-inhibiting effect, such as a diuretic effect, the compounds as described above can be administered orally or parenterally, for example, intramuscularly and subcutaneously, to a patient in need of treatment. The term patient is taken to mean a warm-blooded mammal such as rats, mice, dogs, cats, horses, pigs, cows, sheep and humans. The compounds of the invention can be administered alone or suitably admixed in the form of a pharmaceutical preparation to the patient being treated. The amount of compound administered will vary with the severity of the condition and repetitive treatment may be desired. For oral and parenteral administration, the amount of compound administered, that is, the diuretic effective amount, is from 0.1 to 150 mg/kg of body weight per day and preferably from 1 to 50 mg/kg of body weight per day. Unit dosages for oral or parenteral administration may contain, for example, from 5 to 200 mg of the active ingredient. The compounds can be administered alone or in combination with one another, or in combination with other diuretics.

In practicing the method of this invention, the active ingredient is preferably incorporated in a composition containing a pharmaceutical carrier and from about 5 to about 90% by weight of the cyclopropylamino steroid or a pharmaceutically-acceptable salt thereof. The term "pharmaceutical carrier" refers to known pharmaceuticals excipients useful in formulating pharmaceutically active compounds for internal administration to animals, and which are substantially non-toxic and non-sensitizing under conditions of use. The compositions can be prepared by known techniques for the preparation of tablets or capsules and can contain suitable excipients known to be useful in the preparation of the particular type of composition desired. Suitable pharmaceutical carriers in formulation techniques are found in standard texts, such as Remingtons Pharmaceutical Sciences, Mack Publishing Company, Easton, Pa.

The following examples are presented to illustrate the present invention but they should not be construed as limiting it in any way.

EXAMPLE 1

To a solution of 21 g of dehydroepiandrosterone in a mixture of 175 ml of cyclopropylamine and 150 ml of methanol was added 5 g of molecular sieves The reaction mixture was refluxed for 48 hours, cooled to room temperature, and filtered through magnesium sulfate. The magnesium sulfate was washed with ethyl acetate and the solvent was removed from the combined filtrates under reduced pressure to give 17-(cyclopropylimino)androst-5-en-3$\beta$-ol melting at about 187° C.

EXAMPLE 2

To a solution of 9.1 g of 17-(cyclopropylimino)androst5-en-3$\beta$-ol in 200 ml of dry ethanol was added 2 g of sodium borohydride. The reaction mixture was stirred at room temperature for 3 hours and then 100 ml of solvent was removed from the mixture under reduced pressure The reaction mixture was then quenched with dilute acetic acid, diluted with 600 ml of water, and the pH was adjusted to 14 by the addition of sodium hydroxide. The aqueous mixture was extracted 3 times with 600 ml potions of ethyl acetate and the combined organic extracts were dried over magnesium sulfate. Removal of the solvent under reduced pressure gave the desired 17$\beta$-(cyclopropylamino)androst-5-en-3$\beta$-ol as a white solid; MS (m/z): 370 (M+41)$^+$, 358 (M+29)$^+$, 330(M+H)$^+$, 312 (MH-H$_2$O)$^+$.

EXAMPLE 3

Reaction of dehydroepiandrosterone with 1-methylcyclopropylamine according to the procedure described in Example 1 gives 17-(1-methylcyclopropylimino)androst-5-en-3$\beta$-ol. This is then reduced with sodium borohydride according to the procedure in Example 2 to give 17$\beta$-(1-methylcyclopropylamino)androst-5-en-3$\beta$-ol.

EXAMPLE 4

To a mixture of 10 ml of formic acid and 5 ml of formaldehyde was added 1.4 g of 17$\beta$-(cyclopropylamino)androst-5-en-3$\beta$-ol. The mixture was heated at reflux for 5 hours, the volume was then reduced to 7.5 ml in vacuo, and 10 ml of 50% (w/w) aqueous sodium hydroxide was added. The aqueous layer was separated and extracted with ethyl acetate and the combined organic extracts were dried over magnesium sulfate The solvent was then removed in vacuo and the product was purified by flash chromatography to give 17$\beta$-[N-methyl(cyclopropylamino)]androst-5-en-3$\beta$-ol.

EXAMPLE 5

A solution of 1.5 grams of 17$\beta$-(cyclopropylamino)androst-5-en-3$\beta$-ol in 80 ml of toluene was concentrated to 75% of its original volume and 20 ml of cyclohexanone was added. The mixture was again concentrated to 75% of its volume and 1.5 g of aluminum isopropoxide was added. The reaction mixture was refluxed for 45 minutes, cooled to room temperature, and 50 ml of water and 5 ml of concentrated hydrochloric acid were added. The solution was then treated with 11 g of sodium hydroxide and the two phases were separated. The aqueous phase was extracted with 50 ml of ethyl acetate and the combined organic extracts were dried over sodium sulfate. The solvent was removed in vacuo and crystallization of the residue from hexane/ethyl acetate gave 17$\beta$-(cyclopropylamino)androst-4-en-3-one. MS (m/z): 327 (M+), 312 (M+—CH$_3$). This compound has the following structural formula:

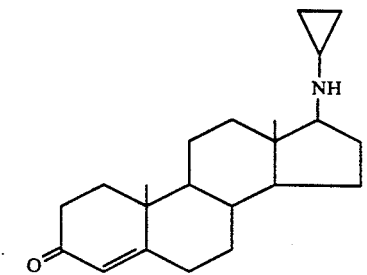

EXAMPLE 6

When the procedure of Example 5 was repeated using 17β-[N-methyl(cyclopropylamino)]androst-5-en-3β-ol, the product obtained was 17β-[N-methyl(cyclopropylamino)]androst-4-en-3-one. MS (CI/CH₄): 342 (M+$^H$).

What is claimed is:

1. A compound which has the formula:

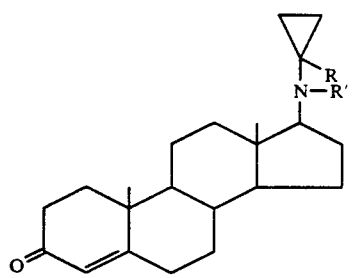

wherein R is hydrogen or methyl; and R' is hydrogen, $C_1$-$C_4$ alkyl or cyclopropyl.

2. A compound according to claim 1 which has the formula:

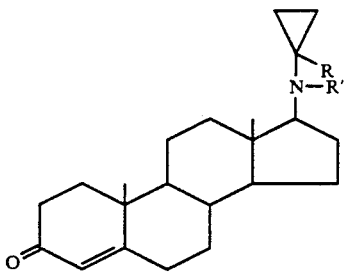

wherein R is hydrogen or methyl; and R' is hydrogen or $C_1$-$C_4$ alkyl.

3. A compound according to claim 1 which is 17β-(cyclopropylamino)androst-4-en-3-one.

4. A compound according to claim 1 which is 17β-[N-methyl(cyclopropylamino)]androst-4-en-3-one.

* * * * *